(12) United States Patent
Mumaw et al.

(10) Patent No.: US 10,470,758 B2
(45) Date of Patent: Nov. 12, 2019

(54) SUTURING DEVICE

(71) Applicant: Ethicon LLC, Guaynabo, PR (US)

(72) Inventors: Daniel J. Mumaw, Cincinnati, OH (US); Frederick E. Shelton, IV, Hillsboro, OH (US)

(73) Assignee: Ethicon LLC, Guaynabo, PR (US)

( * ) Notice: Subject to any disclaimer, the term of this patent is extended or adjusted under 35 U.S.C. 154(b) by 255 days.

(21) Appl. No.: 15/689,488

(22) Filed: Aug. 29, 2017

(65) Prior Publication Data

US 2019/0059877 A1 Feb. 28, 2019

(51) Int. Cl.
*A61B 17/04* (2006.01)
*A61B 17/062* (2006.01)
*A61B 17/06* (2006.01)
*A61B 34/30* (2016.01)
*A61B 17/00* (2006.01)
*A61B 90/00* (2016.01)

(52) U.S. Cl.
CPC ........ *A61B 17/0469* (2013.01); *A61B 17/062* (2013.01); *A61B 17/06133* (2013.01); *A61B 34/30* (2016.02); *A61B 2017/0003* (2013.01); *A61B 2017/00017* (2013.01); *A61B 2017/00398* (2013.01); *A61B 2017/00473* (2013.01); *A61B 2017/00477* (2013.01); *A61B 2017/047* (2013.01); *A61B 2090/031* (2016.02); *A61B 2090/064* (2016.02); *A61B 2090/066* (2016.02)

(58) Field of Classification Search
CPC ............ A61B 17/0469; A61B 17/0482; A61B 17/0491; A61B 17/062; A61B 17/0625; A61B 2017/047; A61B 34/70; A61B 34/74; A61B 34/76
See application file for complete search history.

(56) References Cited

U.S. PATENT DOCUMENTS

| 5,322,055 A | 6/1994 | Davison et al. |
| 5,558,671 A | 9/1996 | Yates |
| 5,792,135 A | 8/1998 | Madhani et al. |

(Continued)

FOREIGN PATENT DOCUMENTS

| WO | WO-2014151621 A1 | 9/2014 |
| WO | WO-2014151952 A1 | 9/2014 |

OTHER PUBLICATIONS

U.S. Appl. No. 15/200,283 entitled "Methods, Systems, and Devices for Initializing a Surgical Tool" filed Jul. 1, 2016.

(Continued)

*Primary Examiner* — Ryan J. Severson
(74) *Attorney, Agent, or Firm* — Mintz Levin Cohn Ferris Glovsky and Popeo, P.C.

(57) ABSTRACT

Devices, systems, and methods for suturing are provided. In an exemplary embodiment, a surgical suturing system can generally include a shaft with an end effector on a distal end thereof. The end effector can be configured to receive a suture needle driving cartridge. The end effector can selectively drive a suturing needle into tissue to suture tissue or retract the suturing needle out of the tissue. The system can further include a control system configured to operably couple to the at least one motor. The control system can be configured to monitor load as the suturing needle is driven into tissue and to reverse a direction of needle travel in the event that the load exceeds a predetermined threshold.

19 Claims, 10 Drawing Sheets

(56) References Cited

U.S. PATENT DOCUMENTS

| | | | |
|---|---|---|---|
| 5,817,084 A | 10/1998 | Jensen | |
| 5,873,873 A | 2/1999 | Smith et al. | |
| 5,878,193 A | 3/1999 | Wang et al. | |
| 5,980,510 A | 11/1999 | Tsonton et al. | |
| 6,039,735 A | 3/2000 | Greep | |
| 6,066,137 A | 5/2000 | Greep | |
| 6,132,368 A | 10/2000 | Cooper | |
| 6,168,605 B1 | 1/2001 | Measamer et al. | |
| 6,231,565 B1 | 5/2001 | Tovey et al. | |
| 6,325,811 B1 | 12/2001 | Messerly | |
| 6,364,888 B1 | 4/2002 | Niemeyer et al. | |
| 6,500,176 B1 | 12/2002 | Truckai et al. | |
| 6,783,524 B2 | 8/2004 | Anderson et al. | |
| 7,112,201 B2 | 9/2006 | Truckai et al. | |
| 7,125,409 B2 | 10/2006 | Truckai et al. | |
| 7,169,146 B2 | 1/2007 | Truckai et al. | |
| 7,186,253 B2 | 3/2007 | Truckai et al. | |
| 7,189,233 B2 | 3/2007 | Truckai et al. | |
| 7,220,951 B2 | 5/2007 | Truckai et al. | |
| 7,309,849 B2 | 12/2007 | Truckai et al. | |
| 7,311,709 B2 | 12/2007 | Truckai et al. | |
| 7,354,440 B2 | 4/2008 | Truckal et al. | |
| 7,380,696 B2 | 6/2008 | Shelton, IV et al. | |
| 7,381,209 B2 | 6/2008 | Truckai et al. | |
| 7,404,508 B2 | 7/2008 | Smith et al. | |
| 7,455,208 B2 | 11/2008 | Wales et al. | |
| 7,506,790 B2 | 3/2009 | Shelton, IV | |
| 7,524,320 B2 | 4/2009 | Tierney et al. | |
| 7,549,564 B2 | 6/2009 | Boudreaux | |
| 7,559,450 B2 | 7/2009 | Wales et al. | |
| 7,654,431 B2 | 2/2010 | Hueil et al. | |
| 7,691,098 B2 | 4/2010 | Wallace et al. | |
| 7,780,054 B2 | 8/2010 | Wales | |
| 7,784,662 B2 | 8/2010 | Wales et al. | |
| 7,798,386 B2 | 9/2010 | Schall et al. | |
| 7,806,891 B2 | 10/2010 | Nowlin et al. | |
| 7,824,401 B2 | 11/2010 | Manzo et al. | |
| 8,439,910 B2 | 5/2013 | Greep et al. | |
| 8,461,744 B2 | 6/2013 | Wiener et al. | |
| 8,469,252 B2 | 6/2013 | Holcomb et al. | |
| 8,602,286 B2 | 12/2013 | Crainich et al. | |
| 8,684,253 B2 | 4/2014 | Giordano et al. | |
| 8,771,270 B2 | 7/2014 | Burbank | |
| 8,986,302 B2 | 3/2015 | Aldridge et al. | |
| 9,023,071 B2 | 5/2015 | Miller et al. | |
| 9,072,536 B2 | 7/2015 | Shelton, IV et al. | |
| 9,095,367 B2 | 8/2015 | Olson et al. | |
| 9,119,657 B2 | 9/2015 | Shelton, IV et al. | |
| 9,168,092 B2 | 10/2015 | Horner et al. | |
| 9,357,998 B2 * | 6/2016 | Martin | A61B 17/0483 |
| 9,393,037 B2 | 7/2016 | Olson et al. | |
| 9,445,816 B2 | 9/2016 | Swayze et al. | |
| 9,585,658 B2 | 3/2017 | Shelton, IV | |
| 9,585,720 B2 * | 3/2017 | Hatakeyama | A61B 34/30 |
| 9,713,468 B2 | 7/2017 | Harris et al. | |
| 9,713,471 B2 | 7/2017 | Holcomb et al. | |
| 9,888,914 B2 * | 2/2018 | Martin | A61B 17/0469 |
| 10,004,491 B2 * | 6/2018 | Martin | A61B 17/0469 |
| 10,182,874 B2 * | 1/2019 | Hasegawa | A61B 1/00 |
| 10,321,905 B2 * | 6/2019 | Martin | A61B 17/0469 |
| 2006/0079874 A1 | 4/2006 | Faller et al. | |
| 2007/0191713 A1 | 8/2007 | Eichmann et al. | |
| 2007/0282333 A1 | 12/2007 | Fortson et al. | |
| 2008/0200940 A1 | 8/2008 | Eichmann et al. | |
| 2010/0191282 A1 | 7/2010 | Harris et al. | |
| 2010/0198248 A1 | 8/2010 | Vakharia | |
| 2011/0015631 A1 | 1/2011 | Wiener et al. | |
| 2011/0087218 A1 | 4/2011 | Boudreaux et al. | |
| 2011/0087256 A1 | 4/2011 | Wiener et al. | |
| 2012/0078139 A1 | 3/2012 | Aldridge et al. | |
| 2012/0078243 A1 | 3/2012 | Worrell et al. | |
| 2012/0078247 A1 | 3/2012 | Worrell et al. | |
| 2012/0116379 A1 | 5/2012 | Yates et al. | |
| 2012/0292367 A1 | 11/2012 | Morgan et al. | |
| 2013/0012957 A1 | 1/2013 | Shelton, IV et al. | |
| 2013/0023868 A1 | 1/2013 | Worrell et al. | |
| 2013/0030428 A1 | 1/2013 | Worrell et al. | |
| 2013/0261648 A1 | 10/2013 | Laurent et al. | |
| 2013/0325034 A1 | 12/2013 | Schena et al. | |
| 2014/0005718 A1 | 1/2014 | Shelton, IV et al. | |
| 2014/0151952 A1 | 6/2014 | Kozaki | |
| 2014/0166728 A1 | 6/2014 | Swayze et al. | |
| 2014/0171970 A1 | 6/2014 | Martin et al. | |
| 2014/0263541 A1 | 9/2014 | Leimbach et al. | |
| 2014/0276931 A1 | 9/2014 | Parihar et al. | |
| 2015/0094737 A1 * | 4/2015 | Hatakeyama | A61B 34/30 606/130 |
| 2015/0209059 A1 | 7/2015 | Trees et al. | |
| 2015/0209573 A1 | 7/2015 | Hibner et al. | |
| 2015/0272575 A1 | 10/2015 | Leimbach et al. | |
| 2015/0282825 A1 | 10/2015 | Trees et al. | |
| 2015/0365296 A1 | 12/2015 | Bunte et al. | |
| 2016/0019918 A1 | 1/2016 | Juman | |
| 2016/0019919 A1 | 1/2016 | Gale et al. | |
| 2016/0089533 A1 | 3/2016 | Turner et al. | |
| 2016/0175060 A1 | 6/2016 | Park | |
| 2016/0287252 A1 | 10/2016 | Parihar | |
| 2016/0361055 A1 * | 12/2016 | Martin | A61B 17/0469 |
| 2016/0367243 A1 | 12/2016 | Martin et al. | |
| 2016/0374772 A1 * | 12/2016 | Hasegawa | A61B 1/00 606/130 |
| 2017/0056038 A1 | 3/2017 | Hess et al. | |
| 2017/0112487 A1 * | 4/2017 | Martin | A61B 17/0469 |
| 2017/0112489 A1 * | 4/2017 | Shelton, IV | A61B 17/0469 |
| 2017/0112493 A1 * | 4/2017 | Bookbinder | A61B 17/0469 |
| 2017/0196637 A1 | 7/2017 | Shelton, IV et al. | |
| 2017/0202609 A1 | 7/2017 | Shelton, IV et al. | |
| 2018/0199932 A1 * | 7/2018 | Martin | A61B 17/0469 |
| 2018/0199934 A1 * | 7/2018 | Martin | A61B 17/0491 |
| 2019/0059877 A1 * | 2/2019 | Mumaw | A61B 17/0469 |

OTHER PUBLICATIONS

U.S. Appl. No. 15/237,653 entitled "Methods, Systems, and Devices for Controlling a Motor of a Robotic Surgical System" filed Aug. 16, 2016.

U.S. Appl. No. 15/422,767 entitled "Robotic Surgical System and Methods for Articulation Calibration" filed Feb. 2, 2017.

U.S. Appl. No. 15/634,620 entitled "Surgical Stapler with Independently Actuated Drivers to Provide Varying Staple Heights" filed Jun. 27, 2017.

U.S. Appl. No. 15/674,075 entitled "Clip Retention for Surgical Clip Applier" filed Aug. 10, 2017.

U.S. Appl. No. 15/674,086 entitled "Surgical Clip Applier Jaw Alignment" filed Aug. 10, 2017.

U.S. Appl. No. 15/674,096 entitled "Surgical Device with Overload Mechanism" filed Aug. 10, 2017.

U.S. Appl. No. 15/674,121 entitled "Jaw for Clip Applier" filed Aug. 10, 2017.

U.S. Appl. No. 15/674,125 entitled "Clip Appliers with Extended Jaw Tip" filed Aug. 10, 2017.

U.S. Appl. No. 15/674,166 entitled "Surgical Clip Applier" filed Aug. 10, 2017.

U.S. Appl. No. 15/689,072 entitled "Methods, Systems, and Devices for Controlling Electrosurgical Tools" filed Aug. 29, 2017.

U.S. Appl. No. 29/613,511 entitled "Clip Applier Rotation Knob" filed Aug. 10, 2017.

* cited by examiner

SUTURING DEVICE

FIELD

Surgical devices and methods are provided for suturing tissue in minimally-invasive surgery.

BACKGROUND

More and more surgical procedures are being performed using electrically-powered surgical devices that are either hand-held or that are coupled to a surgical robotic system. Such devices generally include one or more motors for driving various functions on the device, such as shaft rotation, articulation of an end effector, scissor or jaw opening and closing, firing or clips, staples, cutting elements, and/or energy, etc.

A common concern with electrically-powered surgical devices is the lack of control and tactile feedback that is inherent to a manually-operated device. Surgeons and other users accustomed to manually-operated devices often find that electrically-powered devices reduce their situational awareness because of the lack of feedback from the device. For example, electrically-powered devices do not provide users with any feedback regarding the progress of a cutting and/or sealing operation (e.g., an actuation button or switch is typically binary and provides no feedback on how much tissue has been cut, etc.) or the forces being encountered (e.g., toughness of the tissue). This lack of feedback can produce undesirable conditions. For example, if a motor's power is not adequate to perform the function being actuated, the motor can stall out. Without any feedback to a user, the user may maintain power during a stall, potentially resulting in damage to the device and/or the patient. Furthermore, even if the stall is discovered, users often cannot correct the stall by reversing the motor because a greater amount of force is available to actuate than may be available to reverse it (e.g., due to inertia when advancing). As a result, time-intensive extra operations can be required to disengage the device from the tissue.

In addition, electrically-powered devices can be less precise in operation than manually-operated devices. For example, users of manually-operated devices are able to instantly stop the progress of a mechanism by simply releasing the actuation mechanism. With an electrically-powered device, however, releasing an actuation button or switch may not result in instantaneous halting of a mechanism, as the electric motor may continue to drive the mechanism until the kinetic energy of its moving components is dissipated. As a result, a mechanism may continue to advance for some amount of time even after a user releases an actuation button.

Accordingly, there remains a need for improved devices and methods that address current issues with electrically-powered surgical devices.

SUMMARY

Surgical devices and methods for suturing tissue in minimally-invasive surgery are provided herein. In one aspect, a surgical system is provided that includes a surgical tool with a shaft and an end effector formed at a distal end thereof. The end effector is configured to selectively drive a suturing needle into tissue to effect tissue suturing. The system also has a controller configured to monitor load as the suturing needle is driven into tissue and to reverse a direction of needle travel in the event that the load exceeds a predetermined threshold as the needle is driven into tissue.

The system can have numerous variations. For example, the controller can be configured to monitor an initial advancement load on the needle. In another example, the controller can be configured to monitor the load on the needle relative to where the needle is in a suturing stroke. In still another example, the surgical system can include a robotic drive system that includes the controller. The surgical tool can be coupled to the robotic drive system, and the controller can be configured to monitor a load on a point of coupling between the surgical tool and the robotic drive system. In another example, the surgical system can include a motor operably connected to and controlled by the controller. In one example, the system can include a suture needle driving cartridge that includes the needle. In still another example, the needle driving cartridge includes opposed rollers configured to engage the needle therebetween and to selectively drive the needle clockwise and counterclockwise. In some examples, the end effector can be configured to selectively drive the suturing needle in a circular needle path.

In another embodiment, a surgical system is provided that includes an electromechanical tool with an instrument shaft and an end effector formed on the instrument shaft. The end effector is configured to selectively drive a suturing needle in a suturing direction and a reverse direction. The system also includes an electromechanical arm configured for movement with respect to multiple axes. The electromechanical tool is configured to be mounted on, and move relative to, the electromechanical arm. The system also has a control system that is configured to monitor load as the suturing needle is driven into tissue in the suturing direction and cause the suturing needle to move in the reverse direction in response a monitored load in excess of a threshold limit.

The system can vary in several ways. For example, the control system can be configured to monitor an initial advancement load on the needle. In another example, the control system can be configured to monitor the load on the needle relative to where the needle is in a suturing stroke. In still another example, the control system can be configured to monitor a load on a point of connection between electromechanical tool and the electromechanical arm. In some examples, the system can include a motor operably connected to and controlled by the control system. The motor can be configured to selectively drive the suturing needle. In another example, the system includes a suture needle driving cartridge with the needle. The end effector can be configured to receive the suture needle driving cartridge. In one example, the needle driving cartridge includes opposed rollers configured to engage the needle therebetween and to selectively drive the needle in the suturing direction and the reverse direction.

In another aspect, a surgical method is provided that includes driving a suturing needle into tissue in a first direction using a powered surgical tool, monitoring load as the suturing needle is passed into tissue; and reversing a direction of needle travel if the load exceeds a predetermined threshold as the needle is driven into tissue.

The method can have numerous variations. For example, the method can include allowing the suturing needle to only suture tissue in the first direction. In another example, monitoring load as the suturing needle is passed into tissue can include monitoring an initial advancement load on the needle. In still another example, monitoring load as the suturing needle is passed into tissue can include monitoring the load on the needle relative to where the needle is in a suturing stroke.

BRIEF DESCRIPTION OF DRAWINGS

This invention will be more fully understood from the following detailed description taken in conjunction with the accompanying drawings, in which.

DETAILED DESCRIPTION

Figure 1:
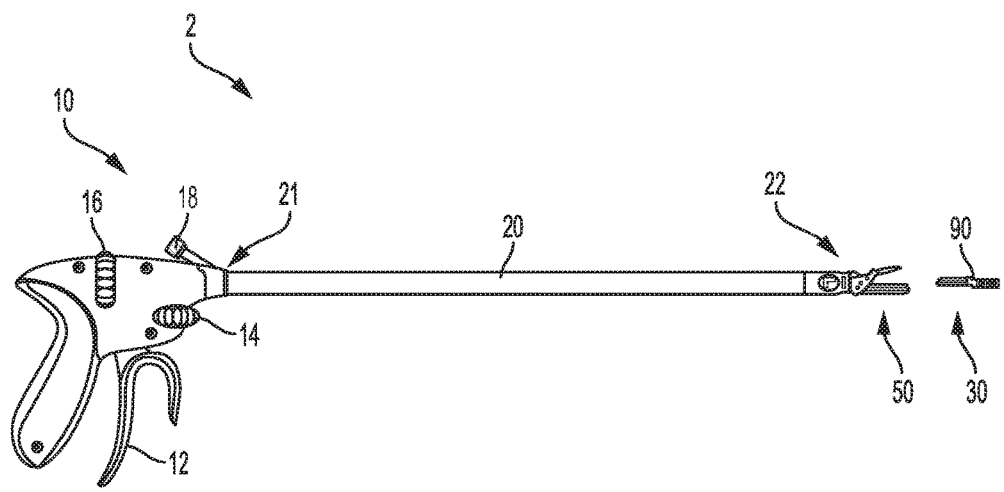
FIG. 1 is one embodiment of a side view of a surgical suturing tool.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices, systems, and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Further, in the present disclosure, like-named components of the embodiments generally have similar features, and thus within a particular embodiment each feature of each like-named component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. Sizes and shapes of the systems and devices, and the components thereof, can depend at least on the anatomy of the subject in which the systems and devices will be used, the size and shape of components with which the systems and devices will be used, and the methods and procedures in which the systems and devices will be used.

It will be appreciated that the terms "proximal" and "distal" are used herein with reference to a user, such as a clinician, gripping a handle of an instrument. Other spatial terms such as "front" and "rear" similarly correspond respectively to distal and proximal. It will be further appreciated that for convenience and clarity, spatial terms such as "vertical" and "horizontal" are used herein with respect to the drawings. However, surgical instruments are used in many orientations and positions, and these spatial terms are not intended to be limiting and absolute.

Devices, systems, and methods for suturing tissue, a vessel, duct, etc. during a surgical procedure are provided. The surgical suturing system generally includes a shaft with an end effector on a distal end thereof. The end effector is configured to receive a suture needle driving cartridge. The end effector can selectively drive a suturing needle into tissue to suture tissue. The system further includes a drive system coupled to the shaft and configured to operably couple to at least one motor for driving the drive system to actuate the suture needle driving cartridge to advance and retract the needle. The system further includes a control system configured to operably couple to the at least one motor. The control system can be configured to actuate the at least one motor to thereby control actuation of the drive system and can enable controlled movement of the suture needle driving cartridge during use of the surgical stapler. In an exemplary embodiment, the control system is configured to monitor load as the suturing needle is driven into tissue and to reverse a direction of needle travel in the event that the load exceeds a predetermined threshold. When the load exceeds a predetermined threshold, the suturing needle may have encountered one or more problems, for example the needle may have encountered particularly thick tissue or a physical obstruction that prevents the needle from being advanced farther. In such a situation, the control system can reverse direction of the needle to allow the needle to be retracted from tissue and, if needed, the end effector can be removed instead of having to physically cut into a patient and withdraw the suturing needle.

An exemplary surgical suturing system can include a variety of features to facilitate application of a surgical suture as described herein and illustrated in the drawings. However, a person skilled in the art will appreciate that the surgical suturing systems can include only some of these features and/or it can include a variety of other features known in the art. The surgical suturing systems described herein are merely intended to represent certain exemplary embodiments. Moreover, while the drive and control systems are shown and described in connection with suturing devices that deploy sutures, a person skilled in the art will appreciate that these systems can be used in connection with other surgical sutures or surgical devices, such as forceps/graspers, needle drivers, scissors, electrocautery tools, clip appliers/removers, suction tools, irrigation tools, etc. Further, a person skilled in the art will appreciate that the surgical suturing systems described herein have application in conventional minimally-invasive and open surgical instrumentation as well as application in robotic-assisted surgery.

Surgical Suturing Device

As indicated above, in an exemplary embodiment control systems are provided for controlling actuation of a surgical suturing device. FIG. 1 illustrates an example of a surgical suturing instrument 2. The instrument 2 comprises a handle assembly 10, an elongate shaft 20, and a cartridge receiving assembly 50, which is operable to receive a needle applier cartridge 30. The shaft 20 has a proximal end 21, a distal end 22, and a longitudinal axis extending therebetween. The handle assembly 10 is connected to the proximal end 21 of the shaft 20. In this example handle assembly 10 is a manual pistol grip handle. However, a variety of other manual actuators could also be used, including but not limited to a scissor grip handle, a syringe grip handle, endoscopic rotary knobs, and the like. The handle assembly 10 could also take the form of a robotic interface, such as a DAVINCI puck, or a housing comprising gears or pulleys, servomechanisms, and the like. The needle applier cartridge 30 is connected to the distal end 22 of shaft 20 via cartridge receiving assembly 50. Needle applier cartridge 30 is operable to rotate an arced needle in a circular path enabling a surgeon to selectively apply sutures. The needle applier cartridge 30 can be provided in a removable and replaceable cartridge body 90 and shaft 20 includes cartridge receiving assembly 50 to releasably hold the cartridge body 90. Versions with reusable components are intended to be cleaned, sterilized, and reused for a multiple surgical procedures, and may include a flush port 18 to facilitate cleaning. A first input 12, shown here as a trigger that pivots between opened and closed positions, can be used to selectively actuate needle applier cartridge 30. The trigger may be spring biased to return the trigger to its open position. A second input 14, shown here as a rotary knob, can be used to selectively articulate shaft 20. A third input 16, shown here as a rotary knob, can be used to selectively rotate the needle applier cartridge 30 about the shaft 20. However, the number, type, configuration, and operation of inputs 12, 14, 16 can vary.

In use, a user can position the needle applier cartridge 30 in a body of a patient by manipulating the rotary knob 14 and the rotary knob 16 against tissue to be sutured. When the needle applier cartridge 30 is positioned as desired, the user can actuate the trigger 12 to selectively actuate needle applier cartridge 30 to complete one suturing stroke. The suturing instrument 2 can then be repositioned and the trigger 14 can be actuated additional times as needed to suture the surgical site.

Additional details on surgical sutures are disclosed in U.S. patent application Ser. No. 14/739,416, filed on Jun. 15, 2015, which is incorporated herein by reference in its entirety.

As discussed above, a user applies manual force to the trigger 14 in order to drive the suturing instrument 2 to deploy sutures into tissue. As such, the suturing instrument 2, as illustrated in FIG. 1, is a manually-operated device. However, more and more surgical procedures are being performed using electrically-powered surgical devices that are either hand-held or that are coupled to a surgical robotic system. Unlike manually-operated devices, electrically-powered surgical devices can lack control and tactile feedback, thereby reducing a surgeon's ability to effectively, accurately, and safely use these devices. Further, manually-operated devices are typically displacement controlled in which mechanical hard stops are used to allow the device to shift to different stages of operation, for example, from a suturing stroke to a return stroke of a suturing needle. However, using mechanical stops has its disadvantages. For example, a user can be limited in attempts to withdraw a suturing needle from tissue without completing a suturing stroke if the needle becomes jammed by striking thick tissue or the housing of the suturing device.

Accordingly various embodiments of drive and control systems are provided for producing real-time feedback during the operation of electrically-powered surgical devices so as to enable a surgeon or other user to effectively and accurately use such devices. In general, the drive system is operably coupled to the suturing assembly and to at least one motor that is configured to drive the suturing needle advancing through a suturing stroke or reversing through a retraction stroke, and the control system is operably coupled to the at least one motor and is configured to actuate the at least motor to drive the drive system and thereby control movement of the suture needle advancing and retracting during suture formation.

Motors/Drive System

Figure 3:
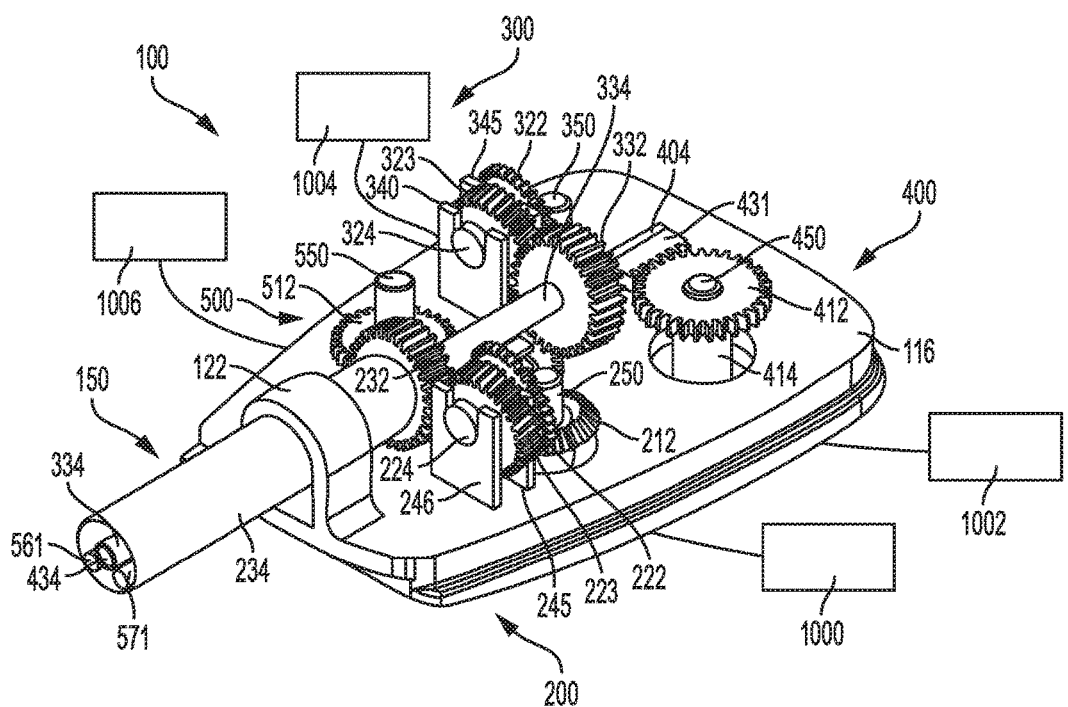
FIG. 3 is a perspective view of an exemplary robotic system drive interface assembly with an outer cover removed that may be used with the robotic system of FIG. 2 in place of the handle assembly.

In general, one or more motors can be used to drive various surgical device functions. The device functions can vary based on the particular type of surgical device, but in general a surgical device can include one or more drive systems that can be configured to cause a particular action or motion to occur, such as shaft and/or end effector rotation, end effector articulation, jaw opening and/or closing, firing to deliver an implantable component such as a suture, clip, staple, adjunct, etc., energy delivery, etc. An exemplary drive system is shown in FIG. 3 and discussed in more detail below. Each drive system can include various components, such as one or more gears that receive a rotational force from the motor(s) and that transfer the rotational force to one or more drive shafts to cause rotary or linear motion of the drive shaft(s). For example, with reference to the drive system 100 that is discussed in more detail below, one or more motors can be coupled to one or more drive assemblies of the drive system to advance the suturing needle. The motor(s) can be located within the surgical device itself or, in the alternative, coupled to the surgical device such as via a robotic surgical system. Each motor can include a rotary motor shaft that is configured to couple to the one or more drive systems of the surgical device so that the motor can actuate the drive system(s) to cause a variety of movements and actions of the device.

It should be noted that any number of motors can be used for driving any one or more drive systems on a surgical device. For example, one motor can be used to actuate two different drive systems for causing different motions. Moreover, in certain embodiments, the drive system can include a shift assembly for shifting the drive system between different modes for causing different actions. A single motor can in other aspects be coupled to a single drive assembly. A surgical device can include any number of drive systems and any number of motors for actuating the various drive systems. The motor(s) can be powered using various techniques, such as by a battery on the device or by a power source connected directly to the device or connected through a robotic surgical system.

Additional components, such as sensors or meter devices, can be directly or indirectly coupled to the motor(s) in order to determine and/or monitor at least one of displacement of a drive system coupled to the motor or a force on the motor during actuation of the drive system. For example, a rotary encoder can be coupled to the motor to monitor the rotational position of the motor, thereby monitoring a rotational or linear movement of a respective drive system coupled to the motor. Alternatively or in addition, a torque sensor can be coupled to the motor to determine or monitor an amount of force being applied to the motor during device operation. It is also contemplated that another way to determine or monitor force on the motor can include measuring current though the motor by using a sensor or a meter device.

In certain embodiments, when the at least one motor is activated, its corresponding rotary motor shaft drives the rotation of at least one corresponding gear assembly located within the drive system of the surgical device. The corresponding gear assembly can be coupled to at least one corresponding drive shaft, thereby causing linear and/or rotational movement of the at least corresponding drive shaft. While movement of two or more drive shafts can overlap during different stages of operation of the drive system, each motor can be activated independently from each other such that movement of each corresponding drive shaft does not necessarily occur at the same time or during the same stage of operation.

When the at least one drive shaft is being driven by its corresponding motor, a rotary encoder, if used, can determine the rotational position of the motor, thereby indicating linear or rotational displacement of the at least one drive shaft. Additionally or in the alternative, when the corresponding motor is activated, the torque sensor, if used, can determine the force on the motor during linear or rotary movement of the at least one drive shaft.

Figure 2:
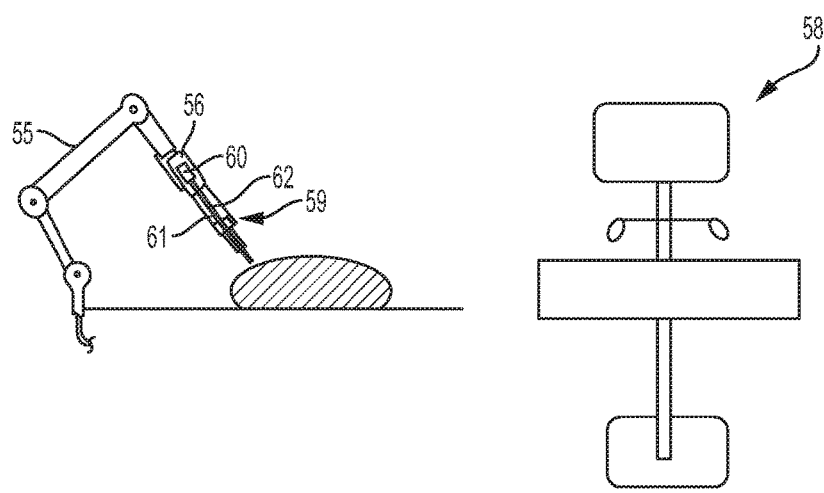
FIG. 2 is a perspective view of an exemplary embodiment of a surgical robotic system that includes a robotic arm having a drive system mounted in a motor housing on an end of the robotic arm, and being wirelessly coupled to a control system.

As indicated above, the motors as well as the control system can be disposed within the handle housing, like the handle assembly 10 shown in FIG. 1, or can be located outside of the handle housing, such as within a surgical robotic system. For example, FIG. 2 illustrates a robotic arm 55 wirelessly coupled to a control system 58 having a console with a display and two user input devices. One or more motors (not shown) are disposed within a motor housing 56 that is coupled to an end of the robotic arm 55. A tool or drive system housing 60 on a surgical tool can house a drive system (not shown) and it can be mounted to the motor housing 56 to thereby operably couple the motor(s) to the drive system. As a result, when the motors are activated by the control system, the motor(s) can actuate the drive system. As shown in FIG. 2, a suture shaft assembly 62 extends from the tool housing 60. During surgery, the staple shaft assembly 62 can be placed within and extend through a trocar 59 that is mounted on the bottom of a carrier 61 extending between the motor housing 56 and a trocar support. The carrier 61 allows the tool to be translated into and out of the trocar 59.

FIGS. 2-7 illustrate a robotic drive system 100 for a suturing end effector (described in detail below). Drive system 100 includes a base 116 with a plurality of apertures 110, a shaft support structure 122, and four drive discs 120*a*, 120*b*, 120*c*, 120*d*. The drive system 100 can be coupled to one or more motors (for example, motors 1000, 1002, 1004, 1006) that are operably coupled to a control system, such as the control system 58. A person skilled in the art will appreciate that the motors and control system can be located within the base 116 to form a powered hand-held device, or they can be located external of the base 116, such as in a robotic system as described with respect to FIG. 2.

While the drive system 100 can have a variety of configurations, in this exemplary embodiment, the drive system 100 includes four drive assemblies: a sheath rotation drive 200 configured to cause rotation, a cartridge receiving assembly rotation drive 300 configured to rotate an end effector at a distal end of the drive system 100, a needle drive 400 configured to cause needle rotation and subsequently a suture stroke, and an articulation drive 500 to articulate an end effector. Each drive assembly, which is discussed in more detail below, can be coupled to a rotary motor shaft of a corresponding motor. During actuation, the corresponding motor can actuate each drive assembly. Further, as described above, one or more motors can be coupled to a corresponding rotary encoder that provides displacement information to the control system 58 for at least one of the sheath rotation drive 200, the cartridge receiving assembly rotation drive 300, the needle drive 400, and the articulation drive 500. Alternatively or in addition, the one or more motors can be coupled to a corresponding torque sensor that provides the control system 58 with information about the amount of force being applied to the motor(s) during operation of the drive system 100.

Exemplary motors for use with the systems disclosed herein are described, for example, in U.S. Pat. Nos. 9,445, 816 and 9,585,658 and in U.S. Patent Publication Nos. 2012/0292367, 2013/0325034, and 2015/0209059.

A shaft assembly 150 extends distally from drive system 100 and includes an outer sheath 234. Shaft support structure 122 extends upwardly from base 116 and provides support to outer sheath 234 such that the outer sheath 234 can still rotate. In some embodiments, shaft support structure 122 can include a bushing, bearings, and/or other features that facilitate rotation of the outer sheath 234 relative to the support structure 122.

Figure 4:
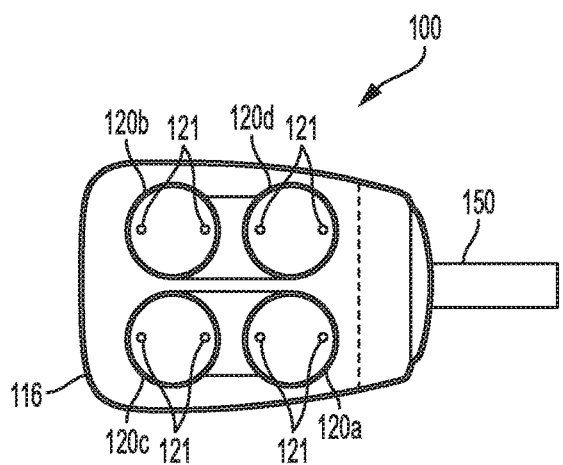
FIG. 4 is a bottom view of the drive interface assembly of FIG. 3.

As shown in FIG. 4, in some embodiments the base 116 also includes the four drive discs 120*a*, 120*b*, 120*c*, 120*d* that are rotatable relative to the plate 116. Each disc 120*a*, 120*b*, 120*c*, 120*d* includes a pair of unitary pins 121 that couple with complementary recesses (not shown) in drive elements of a robotic arm (such as the robotic arm 55). A drive shaft 250, 350, 450, 550 extends upwardly from and perpendicular to each disc 120*a*, 120*b*, 120*c*, 120*d*. As will be described in greater detail below, the discs 120*a*, 120*b*, 120*c*, 120*d* are operable to provide independent rotation of the sheath rotation drive 200, the cartridge receiving assembly rotation drive 300, the need drive 400, and the articulation drive 500 through independent rotation of the drive shafts 250, 350, 450, 550.

Sheath Rotation Drive

Figure 5:
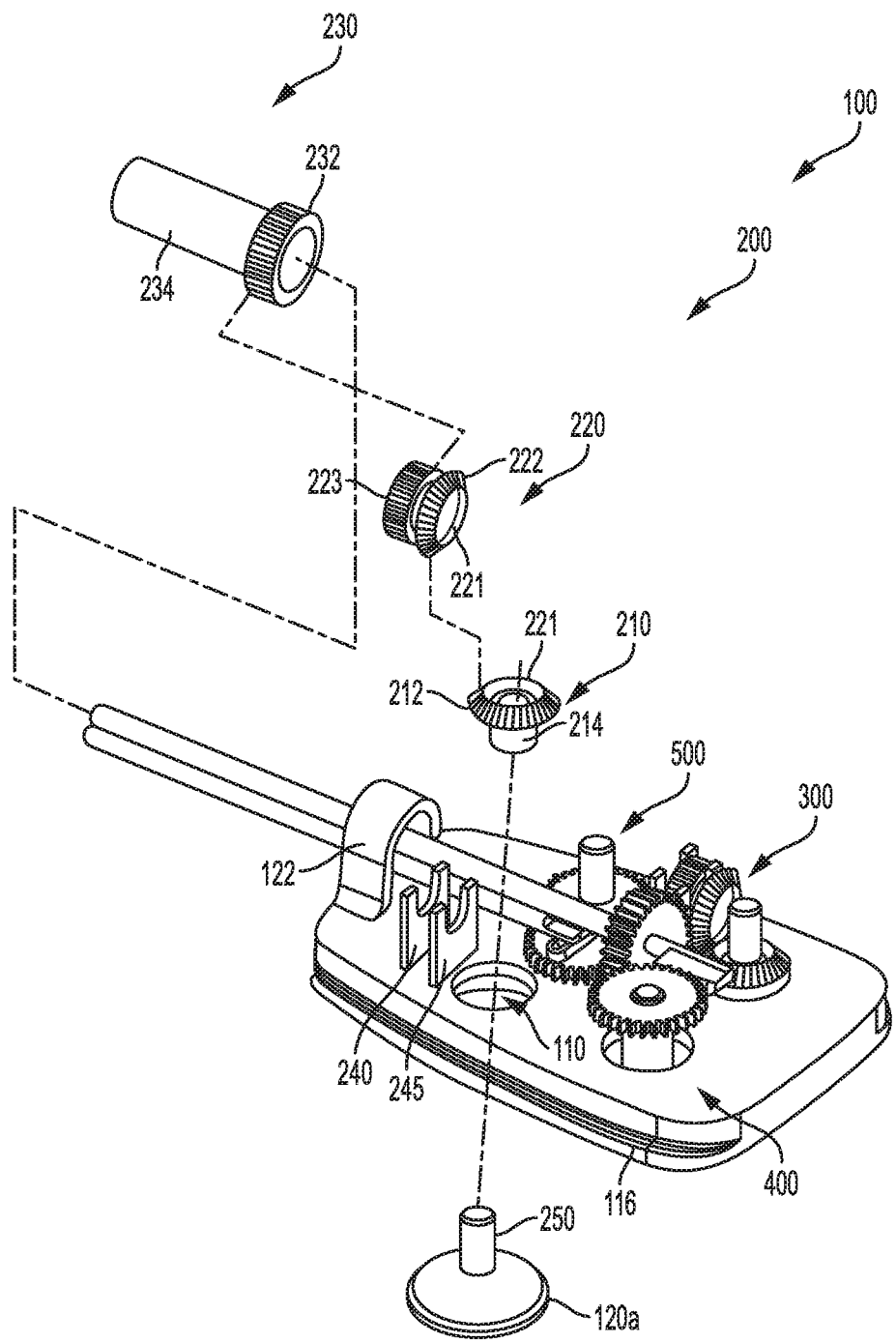
FIG. 5 is a perspective view of the drive interface assembly of FIG. 3 with shaft rotation drive components shown exploded from the rest of the drive interface assembly.

While the sheath rotation drive 200 can have a variety of configuration, in some implementations as shown in FIG. 5, the sheath rotation drive 200 can include the drive disc 120*a*, the drive shaft 250, a first rotary member 210, an idler member 220, and a second rotary member 230. The first rotary member 210 includes a first bevel gear 212 unitarily fixed to a coupling shaft 214. The coupling shaft 214 extends through the aperture 110. The first bevel gear 212 and the coupling shaft 214 together define a bore 211. The bore 211 is dimensioned to receive the drive shaft 250 through an interference fit so that the first rotary member 210 and the drive shaft 250 are coupled together. Rotation of the drive disc 120a is configured to provide rotation to the drive shaft 250 and the first bevel gear 212. The idler member 220 includes a second bevel gear 222 and a first spur gear 223 coupled to each other. Rotation of the second bevel gear 222 is thus configured to rotate the first spur gear 223. The idler member 220 rotatably rests on a pair of legs 240, 245 extending above the base plate 116. The second bevel gear 222 meshes with the first bevel gear 212 such that rotation of the first bevel gear 212 is configured to provide rotation to the second bevel gear 222 and the first spur gear 223. The second rotary member 230 includes a second spur gear 232 and an elongated outer sheath 234, and any rotation of the second spur gear 232 is configured to rotate the elongated outer sheath 234. The first spur gear 223 is positioned to mesh with the second spur gear 232 so that rotation of the first spur gear 223 is configured to provide rotation to the second spur gear 232. Rotating the drive disc 120a of the sheath rotation drive 200 is thus configured to rotate, through the series of gears described above, the elongated outer sheath 234, allowing an operator to rotate and maneuver any end effector disposed at a distal end of the elongated outer sheath 234.

Cartridge Receiving Assembly Rotation Drive

The cartridge receiving assembly rotation drive 300 includes the drive disc 120b, the drive shaft 350, a first rotary member 310, an idler member 320, and a second rotary member 330. The first rotary member 310 is configured substantially identical to the first rotary member 210 as described above such that the first rotary member 310 includes a first bevel gear 312 coupled to a coupling shaft 314. The coupling shaft 314 extends through the aperture 110. The first bevel gear 312 and the coupling shaft 314 together define a bore 311. The bore 311 is dimensioned to receive the drive shaft 350 through an interference fit so that the first rotary member 310 and the drive shaft 350 are coupled together such that rotation of the drive disc 120b also provides rotation to the drive shaft 350 and the first bevel gear 312. The idler member 320 is configured substantially similar to the idler member 220 and includes a second bevel gear 322 and a first spur gear 323 coupled to each other by a coupling shaft 324. Rotation of the second bevel gear 322 is configured to rotate the first spur gear 323. The idler member 320 rotatably rests on a pair of legs 340, 345 extending above the base plate 116. The second bevel gear 322 meshes with the first bevel gear 312 such that rotation of the first bevel gear 312 is thus configured to provide rotation to the second bevel gear 322 and the first spur gear 323. The second rotary member 330 includes a second spur gear 332 and a rotational shaft 334. The first spur gear 323 is positioned to mesh with the second spur gear 332 such that rotation of the first spur gear 323 is configured to provide rotation to the second spur gear 332. The second spur gear 332 is coupled to the rotational shaft 334. The rotational shaft 334 extends coaxially through the elongated outer sheath 234 and is configured to rotate independently of the elongated outer sheath 234. The rotational shaft 334 is configured to rotate a cartridge receiving assembly 650 disposed on a distal end of the rotational shaft 334 about a bearing 624 relative to the elongated outer sheath 234. Rotation of the drive disc 120b is thus configured to rotate, through the series of gears described above, the rotational shaft 334 and the cartridge receiving assembly 650.

By way of example only, the distal portion of the rotational shaft 334 can be configured and operable in accordance with at least some of the teachings of U.S. Pub. No. 2014/0171970, entitled "Circular Needle Applier with Articulating and Rotating Shaft," published Jun. 19, 2014, the disclosure of which is incorporated by reference herein.

Articulation Drive

Figure 6:
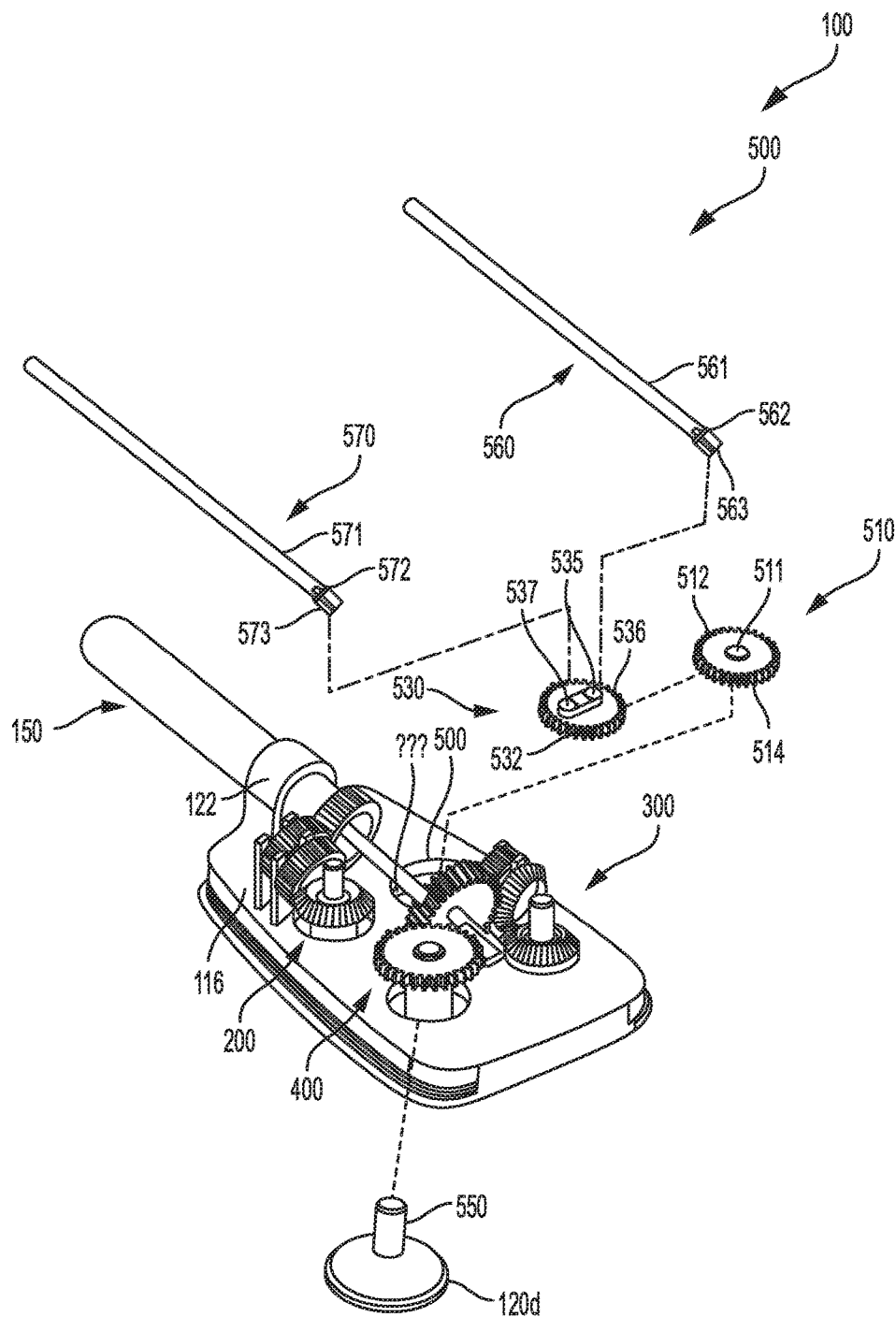
FIG. 6 is a perspective view of the drive interface assembly of FIG. 3 with articulation drive components shown exploded from the rest of the drive interface assembly.

While the articulation drive 500 can have a variety of configurations, in some embodiments, as shown in FIG. 6, the articulation drive 500 can include the drive disc 120d, the drive shaft 550, a rotational member 510, an articulation base 530, and articulation rods 560, 570. The rotational member 510 includes a coupling shaft 514 coupled to a first spur gear 512. A coupling shaft 514 extends through the aperture 110, and the coupling shaft and the first spur gear together define a bore 511. The bore 511 is dimensioned to receive the drive shaft 550 through an interference fit so that the rotational member 510 and the drive shaft 550 are coupled together. Rotation of the drive disc 120d is configured to provide rotation to the drive shaft 510 and the first spur gear 512. The articulation base 530 includes a second spur gear 532, a cam feature 535, and a post 538 extending from the face of the base plate 116. The second spur gear 532 is rotatably supported on the post 538. The first spur gear 512 is in meshing engagement with the second spur gear 532 so that rotation of the first spur gear 512 rotates the second spur gear 532 and the cam feature 535 about the post 538. Rotation of the drive disc 120d thus is configured to provide rotation of the second spur gear 532 and the cam feature 535. Rotation of the first spur gear 512 is configured to be converted in rotation of the second spur gear 532 about an axis defined by the post 538. The post 538 is configured to receive the center of the second spur gear 532 so that the second spur gear 532 can rotate. The cam feature 535 is fixed to the second spur gear 532 such that the cam feature 535 rotates with the second spur gear 532 about the axis defined by the post 538. The cam feature 535 includes two slots 536, 537 laterally spaced from the axis defined by the post 538. The articulation rods 560, 570 include longitudinal members 561, 571 and transverse members 563, 573 respectively. The transverse members 563, 573 are configured to be positioned in respective slots 536, 537. The longitudinal members 561, 571 extend through the elongated outer sheath 234 and terminate distally from the distal end of the elongated outer sheath 234 (as discussed in more detail below) such that rotation of the cam feature 535 will opposingly push and pull the actuation rods 560, 570. The simultaneous push and pull action is configured to articulate the cartridge receiving assembly 650 at the distal end of the elongated outer sheath 234.

Needle Drive

Figure 7:
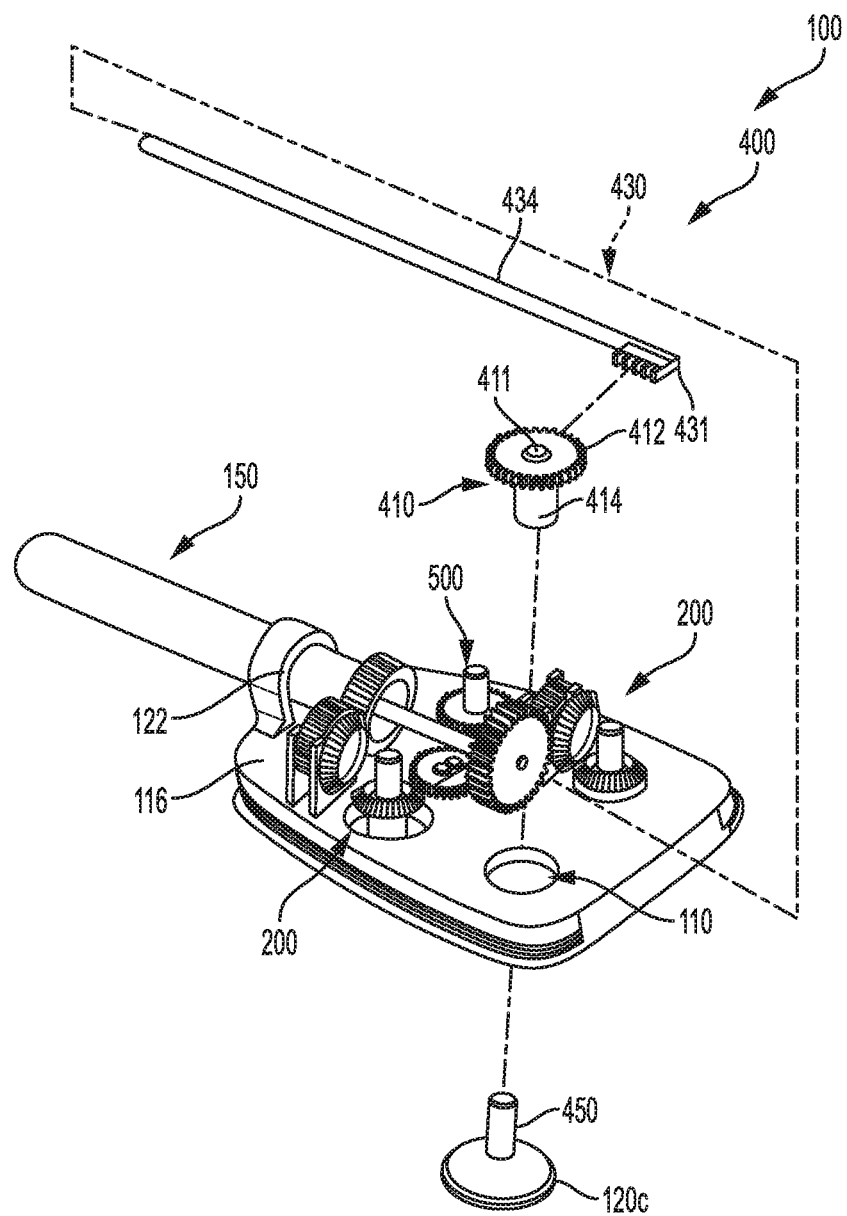
FIG. 7 is a perspective view of the drive interface assembly of FIG. 3 with needle drive components shown exploded from the rest of the drive interface assembly.
Figure 8:
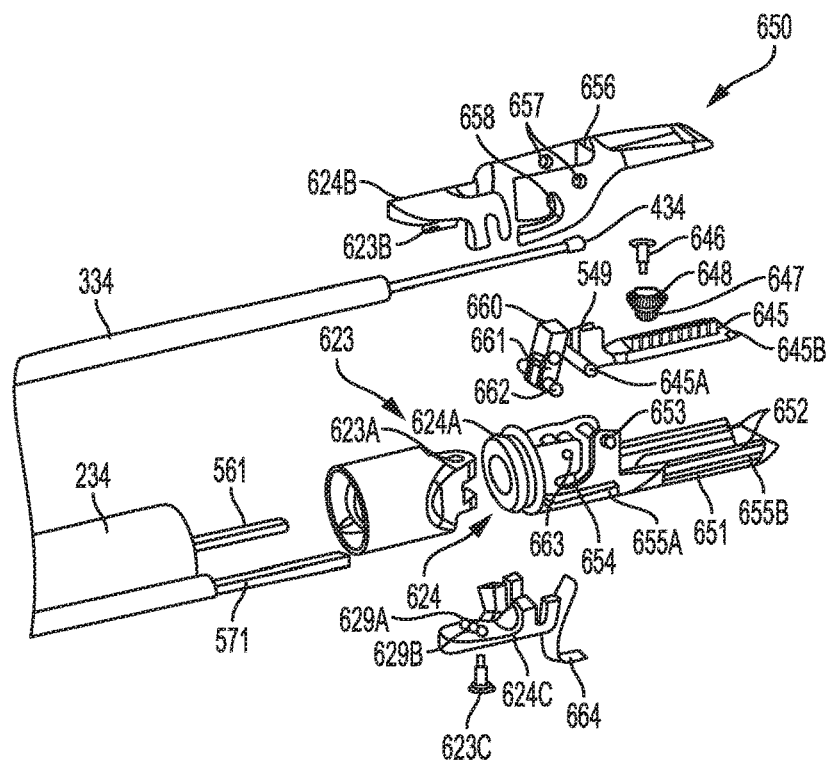
FIG. 8 is a perspective exploded view of a cartridge receiving assembly on a distal end of the drive interface assembly of FIG. 3.

The needle drive 400 can have a variety of configurations. For example, as shown in FIG. 7, the needle drive 400 includes a drive disc 120c, a drive shaft 450, a rotational member 410, and a translation member 430. The rotational member 410 includes a coupling shaft 414 coupled to a pinion 412. The coupling shaft 414 and the pinion 412 together define a bore 411, and the bore 411 is dimensioned to receive the drive shaft 450 through an interference fit so that the rotational member 410 and the drive shaft 450 are coupled together. Any other means of fixing the drive shaft 250 to the first rotary member 210 can be used, such as welding. Rotation of the drive disc 120c is configured to provide rotation to the drive shaft 450 and the pinion 412. The translation member 430 includes a translating rod 434 and a rack 431. The translating rod 434 coaxially extends through both hollow portion 331 and a circumferential flange 624A, and the translating rod 434 is slidably disposed within the hollow portion 331. As shown in FIG. 8, a distal end of the translating rod 434 includes a distal bendable portion 628B coupled to a mount 649. Therefore, translating rod 434 is configured to actuate a needle cartridge body 690. The rack 431 is fixed to the translating rod 434 so that linear movement of the rack 431 creates linear movement of the translating rod 434. Teeth on the rack 431 mesh with teeth on the pinion 412 such that rotation of the pinion 412 provides linear movement of the rack 431. Rotation of the drive disc 120c is configured to rotate the drive shaft 450 and the pinion 412. Rotation of the pinion 412 occurs on an axis defined by the drive shaft 450 so that rotation of the pinion 412 clockwise is configured to create proximal translation of the rack 431 and the translating rod 434 while counterclockwise rotation of the pinion 412 is configured to create distal translation of the rack 431 and the translating rod 434. This linear movement is translated into rotational movement at the cartridge receiving assembly 650 (as discussed below) and results in drive and return strokes of the suturing needle.

Other suitable ways to create a drive stroke and a return stroke will be apparent to those skilled in the art in view of the teachings herein. For example, in some embodiments the translating rod 434 and the rotational shaft 334 can be coupled together such that the translating rod 434 will rotate with the rotational shaft 334 while the translating rod 434 can translate relative to the rotational shaft 334. Thus, when the rotational shaft 334 is driven to rotate as described above, such rotation can be communicated to the cartridge receiving assembly 650 via the translating rod 434, and the translating rod 434 can still freely actuate the needle cartridge body 690 without interference from the rotational shaft 334.

Cartridge Receiving Assembly

Figure 9:
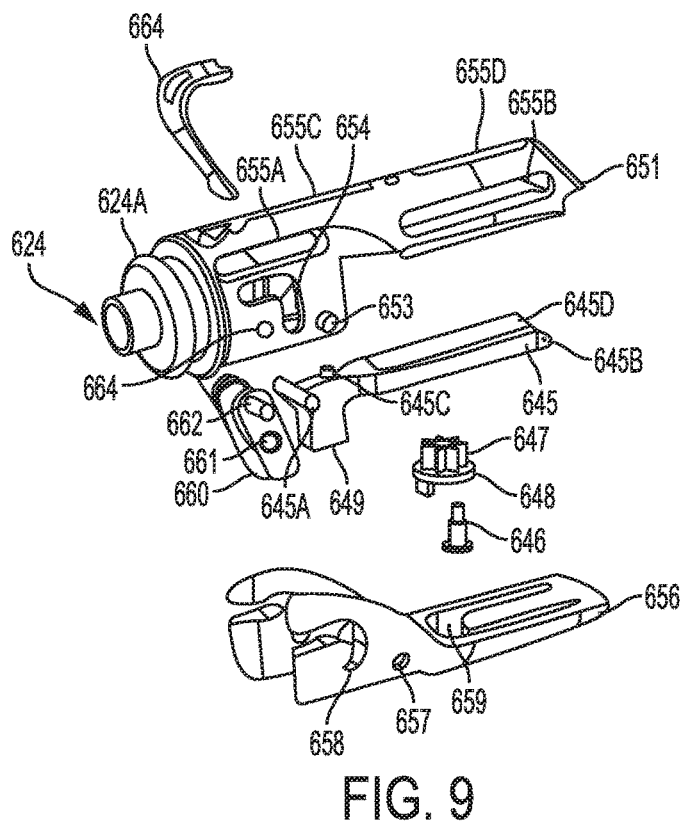
FIG. 9 is a perspective exploded view of the cartridge receiving assembly of FIG. 8.

As illustrated in FIGS. 8-9, the distal end of the outer sheath 234 terminates in an articulation joint 623 and the rotational bearing 624. Articulation joint 623 includes a knuckle 623A that receives pins 623B, 623C, which are connected to bearing supports 624B, 624C, enabling the cartridge receiving assembly 650 to articulate left and right relative the outer sheath 234. The longitudinal members 561, 571 connect to pins 629A, 629B on a bearing support 624C to allow articulation of the cartridge receiving assembly 650 about the joint 623 relative to the outer sheath 234. A rotational bearing 624 is positioned distal to the articulation joint 623. The bearing 624 includes a circumferential flange 624A that is captured between the bearing supports 624B, 624C such that the flange 624A can rotate relative the bearing supports 624B, 624C and enabling unbounded rotation of the cartridge receiving assembly 650 relative to the outer sheath 234. The translating rod 434 extends through the articulation joint 623 and through the bearing 624 to fixedly connect to a mount 649 on a rack 645.

The rack 645 reciprocates longitudinally in a lower jaw 651 with followers 645A, 645B, 645C, 645D constrained in tracks 655A, 655B, 655C, 655D), respectively. The tracks 655A, 655B, 655C, 655D open through the lower jaw 651, providing fluid passages to the internal components within the lower jaw 651 and thus being configured to facilitate easier cleaning. A pinion 647 is mounted to lower jaw 651 by the pin 646 in the rack 645 such that longitudinal reciprocation of the rack 645 by the longitudinal movement of the translating rod 434 is converted into rotational reciprocation of the pinion 647. A key 648 communicates the reciprocating rotation to a rotary input 694 in the cartridge body 690, which actuates the needle 670 in the cartridge body 690.

The cartridge receiving assembly 650 is dimensioned and configured to receive and hold the cartridge body 690. The cartridge receiving assembly 650 has upper and lower jaws 656, 651 that are configured to transition between an open configuration and a closed configuration. The lower jaw 651 has two laterally offset longitudinal rails 652 that are dimensioned and adapted to receive the cartridge body 690. The upper jaw 656 pivots relative to the lower jaw 651 about a pin 653 that is received in holes 657. A tooth 659 is oriented downwardly from the upper jaw 656 toward the lower jaw 651 with a ramped distal face and a stepped proximal face. The tooth 659 is dimensioned and adapted to latch with the cartridge body 690 and longitudinally retain the cartridge body 690 in the jaws 651, 656. A button 660, a spring 664, and a follower 662 with cam slots 654, 658 is operable to open and close the jaws 651, 656. A spring 664 engages and biases the button 660 distally.

Cartridge Body

Figure 10:
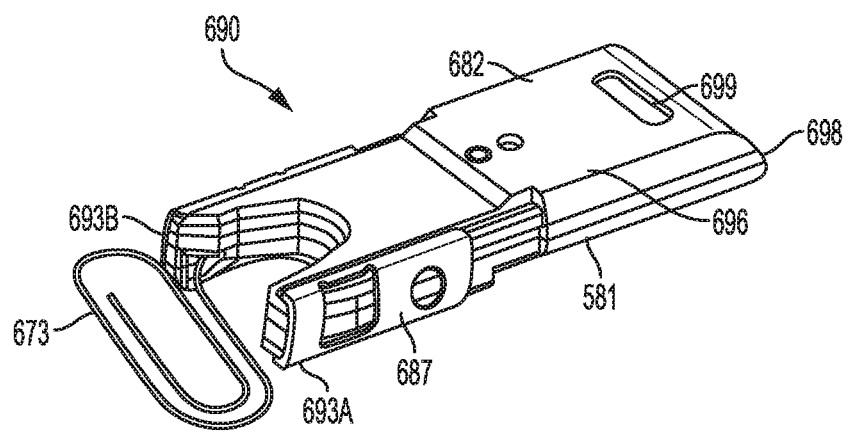
FIG. 10 is a perspective view of an exemplary cartridge configured for receipt in the cartridge receiving assembly of FIG. 8.
Figure 11:
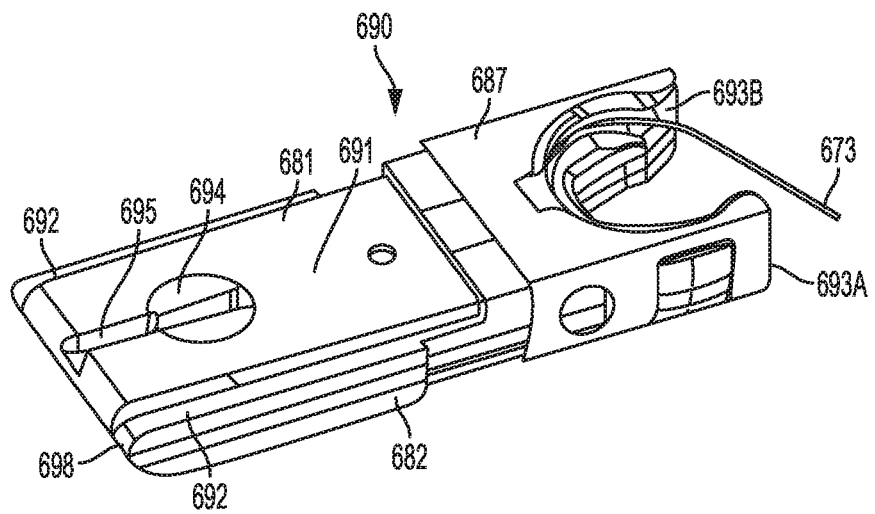
FIG. 11 is a perspective view of the cartridge of FIG. 10.

As illustrated in FIGS. 10 and 11, the cartridge body 690 has a lower face 691 that is configured to engage the lower jaw 651; and an upper face 696 configured to engage the upper jaw 656. The lower face 691 has a pair of longitudinal notched shoulders 692 that are dimensioned to interface and mate with the rails 652 to help to prevent improper insertion of the cartridge body 690 into the cartridge receiving assembly 650. In contrast, the upper face 696 is asymmetrical relative to the lower face 691 and lacks shoulder notches, so the upper face 696 would interfere with the rails 652 if the cartridge body 690 were inserted upside-down in the cartridge receiving assembly 650. Other features can be used to prevent incorrect engagement, such as the geometry of a proximal face 698 of the cartridge body 690. Arms 693A, 693B define a generally U-shaped distal end on cartridge body 690. A slot 695 and a rotary input 694 are aligned and dimensioned to receive the key 648 while the cartridge body 690 is being slid into the cartridge receiving assembly 650. When the cartridge body 690 is fully seated into the cartridge receiving assembly 650, a step 699 aligns with and receives the tooth 659 to latch the cartridge body 690 in the cartridge receiving assembly 650. The key 648 also aligns with the rotary input 694, thereby providing a torsional interface that rotationally couples the pinion 647 and rotary input 694. In use, the needle 670 exits the arm 693A and enters the arm 693B.

Figure 12:
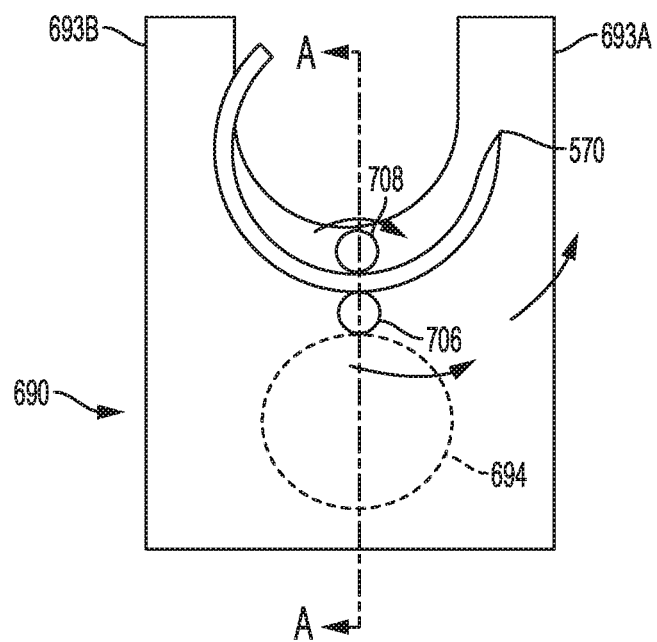
FIG. 12 is a top cross-sectional view of the cartridge of FIG. 10.
Figure 13:
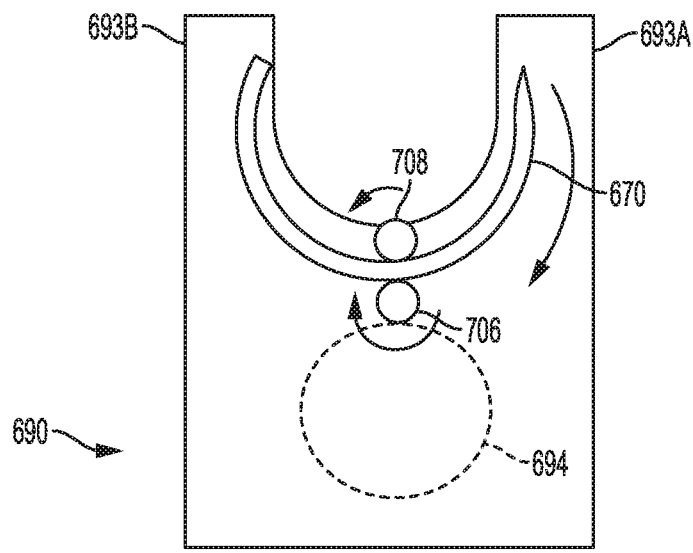
FIG. 13 is a top cross-sectional view of the cartridge of FIG. 10.
Figure 14:
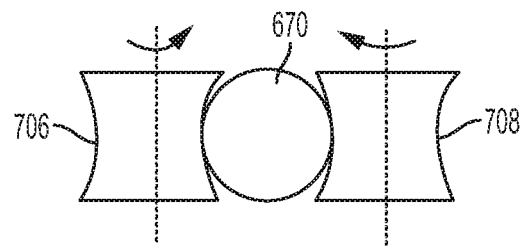
FIG. 14 is a cross-sectional side view of the cartridge of FIG. 10 in the direction A indicated on FIG. 10.

As illustrated in FIGS. 11-13, the cartridge body 690 includes a lower body 681, an upper body 682, and the needle 670. The needle 670 has a leading end 671 and a length of suture 673 extending from a trailing end 672. The needle 670 orbits in a circular path defined by a needle track and between the arms 693A, 693B. The input driver 706 is friction fit against the needle 670 on a proximal side of the needle 670, as illustrated in FIGS. 12-14, and the follow driver 708 is friction fit against the needle 670 on a distal side.

Figure 15:
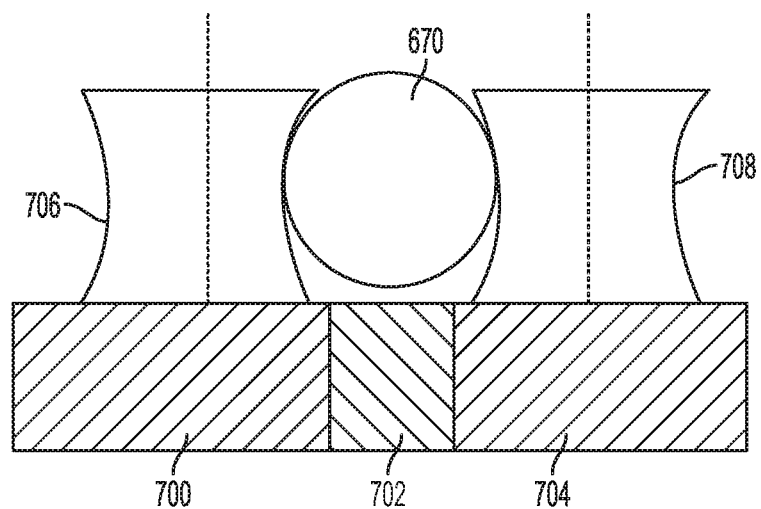
FIG. 15 is a cross-sectional side view of the cartridge of FIG. 10 in the direction A indicated on FIG. 10.

As illustrated in FIG. 15, an input gear 700 coupled with an input driver 706, a connection gear 702, a follow gear 704 coupled with a follow driver 708, and the rotary input 694 are captured between the lower body 681 and the upper body 682. The rotary input 694 is in operational engagement with the input gear 700, which is in operation engagement with the connection gear 702. The connection gear 702 is in turn in operational engagement with the follow gear 704.

In Operation

The gears are thus configured such that rotation of the rotary input 694 will rotate the input gear 700, which will rotate the connection gear 702 that will then rotate the follow gear 704. Because the input driver 706 is coupled to the input gear 700 and the follow driver 708 is coupled to the follow gear 704, rotation of the input gear 700 will rotate the input driver 706 and rotation of the follow gear 704 will rotate the follow driver 708. Because the input and follow drivers 706, 708 are oriented to rotate in opposite directions and because they are in friction fit with the needle 670, rotation of the input and follow drivers 706, 708 will result in advancement or retraction of the needle 670 along the needle path, depending on which direction the input and follow drivers 706, 708 rotate. The input gear 700, the connection gear 702, and the follow gear 704 are all spring biased into engagement with one another to allow for rotation of the input gear 700 to transfer motion to the other two gears 702, 704. However, the connection and follow gears 702, 704 can be pushed out of engagement with the input gear 700 to release friction on the needle 670 and allow the needle 670 to be released and reset at the end of each stroke.

While a specific driving mechanism is provided above for the needle 670, a variety of different driving mechanisms can be used to cause rotation of the input and follow drivers 706, 708, as will be appreciated by one skilled in the art. Clockwise and counterclockwise rotation of the input and follow drivers 706, 708 allow the needle 670 to be advanced forwards such that the tip 671 enters tissue and retracted backwards such that the tip 671 is withdrawn from tissue without completing a suturing stroke. This ability to advance forwards and/or retract backwards allows a user to operate with the needle 670 in normal operating circumstances while being able to withdraw the needle 670 if the need arose without having to disassemble the suturing device and/or cut into the patient.

In operation, a robotic system, such as one that includes robotic arm 55 coupled to the control system 58 discussed above, can control the robotic drive system 100, such as by controlling rotation of the input and follow drivers 706, 708, while monitoring a variety of factors to ensure that the needle 670 advances out of the cartridge body 690 and into tissue correctly. The control system 58 can monitor force and/or lifting load throughout the suturing process, and if an adverse situation is detected during the advancement of the needle 670, the control system 58 can reverse rotational direction of the input and follow drivers 706, 708 and retract the needle back into the cartridge body 690. As discussed above, a variety of components can be used to monitor this information, such as sensors or meter devices that can be directly or indirectly coupled to the motor(s) in order to determine and/or monitor at least one of displacement of a drive system coupled to the motor or a force on the motor during actuation of the drive system. Alternatively or in addition, a torque sensor can be coupled to the motor to determine or monitor an amount of force being applied to the motor during operation.

Specifically, the control system 58 can monitor a variety of different factors, such as too high of an advancement load on the needle 670 at an early stage of the needle advancement stroke, which can indicate that tissue may be too thick, or an irregular load on the needle 670 relative to where the needle 670 is in the needle advancement stroke, which can indicate that the needle 670 has struck an obstacle during advancement such as the housing. The system 58 can also monitor for too high of a perpendicular load on surrounding tissue, which can be determined by the load on the point of connection between the shaft assembly 150 and the drive system 100 and/or the drive system 100 and the robotic arm 55. The system 58 can look for a variety of threshold perpendicular loads, for example in the range of about 0.25 pounds to about 2 pounds. These various loads can be monitored singularly or in any combination by the system.

When used to suture tissue, the cartridge body 690 can be positioned against tissue to be sutured by maneuvering the cartridge body 690 into place through driving the drive discs 120a, 120b, 120d, respectively, to actuate the sheath rotation drive 200, the cartridge receiving assembly rotation drive 300, and the articulation drive 500. Once the cartridge body 690 is positioned, the needle drive 400 can be actuated by driving the drive disc 120c. As the drive disc 120c is rotated by a motor in a robotic system (such as a motor operably coupled to robotic arm 55), the successive gear train in the needle drive 400 will cause linear translation of the translating rod 434, which is converted into rotational reciprocation of the pinion 647 and is communicated to the rotary input 694 in the cartridge body 690. At this point, the needle 670 is actuated and completes a suturing stroke. During the suturing stroke the control system 58 monitors load as the suturing needle 670 is passed into tissue, and the traveling direction of the suturing needle 670 can be reversed if the monitored load exceeds a predetermined threshold, as discussed above. The control system 58 can monitor the suturing stroke in real time and automatically reverse the travel direction if the threshold is exceeded. A user can also manually order the robotic system to reverse direction of the suturing needle 670, if needed.

The same needle driving mechanism including an input gear coupled with an input driver, a connection gear, a follow gear coupled with a follow driver, and a rotary input can be incorporated into a handheld suturing device.

Figure 16:
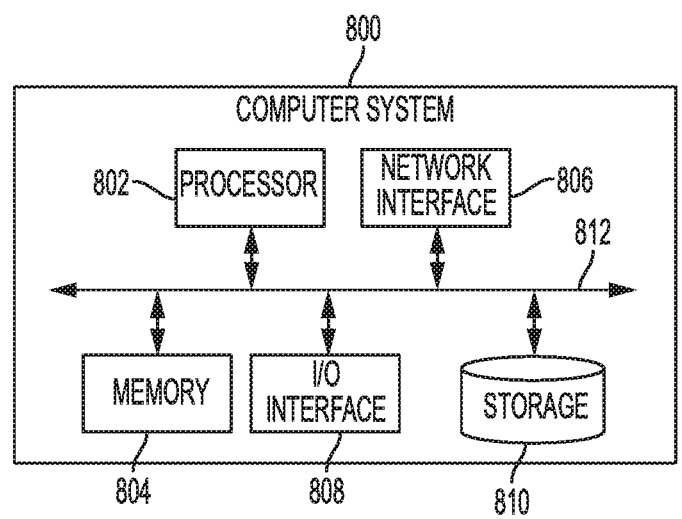
FIG. 16 is an exemplary embodiment of a computer system that can be used to implement a control system of the present disclosure.

FIG. 16 illustrates one exemplary embodiment of a computer system 800. As shown, the computer system 800 includes one or more processors 802 which can control the operation of the computer system 800. "Processors" are also referred to herein as "controllers." The processor(s) 802 can include any type of microprocessor or central processing unit (CPU), including programmable general-purpose or special-purpose microprocessors and/or any one of a variety of proprietary or commercially available single or multi-processor systems. The computer system 800 can also include one or more memories 804, which can provide temporary storage for code to be executed by the processor(s) 802 or for data acquired from one or more users, storage devices, and/or databases. The memory 804 can include read-only memory (ROM), flash memory, one or more varieties of random access memory (RAM) (e.g., static RAM (SRAM), dynamic RAM (DRAM), or synchronous DRAM (SDRAM)), and/or a combination of memory technologies.

The various elements of the computer system 800 can be coupled to a bus system 812. The illustrated bus system 812 is an abstraction that represents any one or more separate physical busses, communication lines/interfaces, and/or multi-drop or point-to-point connections, connected by appropriate bridges, adapters, and/or controllers. The computer system 800 can also include one or more network interface(s) 806, one or more input/output (IO) interface(s)

808 that can include one or more interface components, and one or more storage device(s) 810.

The network interface(s) 806 can enable the computer system 800 to communicate with remote devices, e.g., motor(s) coupled to the drive system 100 that is located within the surgical device or a robotic surgical system or other computer systems, over a network, and can be, for non-limiting example, remote desktop connection interfaces, Ethernet adapters, and/or other local area network (LAN) adapters. The IO interface(s) 808 can include one or more interface components to connect the computer system 800 with other electronic equipment, such as the sensors located on the motor(s). For non-limiting example, the IO interface(s) 808 can include high speed data ports, such as universal serial bus (USB) ports, 1394 ports, Wi-Fi, Bluetooth, etc. Additionally, the computer system 800 can be accessible to a human user, and thus the IO interface(s) 808 can include displays, speakers, keyboards, pointing devices, and/or various other video, audio, or alphanumeric interfaces. The storage device(s) 810 can include any conventional medium for storing data in a non-volatile and/or non-transient manner. The storage device(s) 810 can thus hold data and/or instructions in a persistent state, i.e., the value(s) are retained despite interruption of power to the computer system 800. The storage device(s) 810 can include one or more hard disk drives, flash drives, USB drives, optical drives, various media cards, diskettes, compact discs, and/or any combination thereof and can be directly connected to the computer system 800 or remotely connected thereto, such as over a network. In an exemplary embodiment, the storage device(s) 810 can include a tangible or non-transitory computer readable medium configured to store data, e.g., a hard disk drive, a flash drive, a USB drive, an optical drive, a media card, a diskette, a compact disc, etc.

The elements illustrated in FIG. 16 can be some or all of the elements of a single physical machine. In addition, not all of the illustrated elements need to be located on or in the same physical machine. Exemplary computer systems include conventional desktop computers, workstations, minicomputers, laptop computers, tablet computers, personal digital assistants (PDAs), mobile phones, and the like.

The computer system 800 can include a web browser for retrieving web pages or other markup language streams, presenting those pages and/or streams (visually, aurally, or otherwise), executing scripts, controls and other code on those pages/streams, accepting user input with respect to those pages/streams (e.g., for purposes of completing input fields), issuing HyperText Transfer Protocol (HTTP) requests with respect to those pages/streams or otherwise (e.g., for submitting to a server information from the completed input fields), and so forth. The web pages or other markup language can be in HyperText Markup Language (HTML) or other conventional forms, including embedded Extensible Markup Language (XML), scripts, controls, and so forth. The computer system 800 can also include a web server for generating and/or delivering the web pages to client computer systems.

In an exemplary embodiment, the computer system 800 can be provided as a single unit, e.g., as a single server, as a single tower, contained within a single housing, etc. The single unit can be modular such that various aspects thereof can be swapped in and out as needed for, e.g., upgrade, replacement, maintenance, etc., without interrupting functionality of any other aspects of the system. The single unit can thus also be scalable with the ability to be added to as additional modules and/or additional functionality of existing modules are desired and/or improved upon.

A computer system can also include any of a variety of other software and/or hardware components, including by way of non-limiting example, operating systems and database management systems. Although an exemplary computer system is depicted and described herein, it will be appreciated that this is for sake of generality and convenience. In other embodiments, the computer system may differ in architecture and operation from that shown and described here.

A person skilled in the art will appreciate that the present invention has application in conventional minimally-invasive and open surgical instrumentation as well application in robotic-assisted surgery.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A surgical system, comprising:
   a surgical tool including a shaft and an end effector formed at a distal end thereof, the end effector being configured to selectively drive a suturing needle into tissue to effect tissue suturing; and
   a controller configured to monitor load as the suturing needle is driven into tissue and to reverse a direction of needle travel in the event that the load exceeds a predetermined threshold as the needle is driven into tissue.

2. The surgical system of claim 1, wherein the controller is configured to monitor an initial advancement load on the needle.

3. The surgical system of claim 1, wherein the controller is configured to monitor the load on the needle relative to where the needle is in a suturing stroke.

4. The surgical system of claim 1, further comprising a robotic drive system that includes the controller, the surgical tool being coupled to the robotic drive system, and wherein the controller is configured to monitor a load on a point of coupling between the surgical tool and the robotic drive system.

5. The surgical system of claim 1, further comprising a motor operably connected to and controlled by the controller.

6. The surgical system of claim 1, further comprising a suture needle driving cartridge that includes the needle.

7. The surgical system of claim 6, wherein the needle driving cartridge includes opposed rollers configured to engage the needle therebetween and to selectively drive the needle clockwise and counterclockwise.

8. The surgical system of claim 1, wherein the end effector is configured to selectively drive the suturing needle in a circular needle path.

9. A surgical system, comprising:
an electromechanical tool including an instrument shaft and an end effector formed on the instrument shaft, the end effector being configured to selectively drive a suturing needle in a suturing direction and a reverse direction;
an electromechanical arm configured for movement with respect to multiple axes, wherein the electromechanical tool is configured to be mounted on, and move relative to, the electromechanical arm; and
a control system configured to monitor load as the suturing needle is driven into tissue in the suturing direction and cause the suturing needle to move in the reverse direction in response a monitored load in excess of a threshold limit.

10. The surgical system of claim 9, wherein the control system is configured to monitor an initial advancement load on the needle.

11. The surgical system of claim 9, wherein the control system is configured to monitor the load on the needle relative to where the needle is in a suturing stroke.

12. The surgical system of claim 9, wherein the control system is configured to monitor a load on a point of connection between electromechanical tool and the electromechanical arm.

13. The surgical system of claim 9, further comprising a motor operably connected to and controlled by the control system, the motor being configured to selectively drive the suturing needle.

14. The surgical system of claim 9, further comprising a suture needle driving cartridge that includes the needle, the end effector being configured to receive the suture needle driving cartridge.

15. The surgical system of claim 14 wherein the needle driving cartridge includes opposed rollers in the suture needle driving cartridge configured to engage the needle therebetween and to selectively drive the needle in the suturing direction and the reverse direction.

16. A surgical method, comprising:
driving a suturing needle into tissue in a first direction using a powered surgical tool;
monitoring load as the suturing needle is passed into tissue; and
reversing a direction of needle travel if the load exceeds a predetermined threshold as the needle is driven into tissue.

17. The surgical method of claim 16, wherein the suturing needle only sutures tissue in the first direction.

18. The surgical method of claim 16, wherein monitoring load as the suturing needle is passed into tissue includes monitoring an initial advancement load on the needle.

19. The surgical method of claim 16, wherein monitoring load as the suturing needle is passed into tissue includes monitoring the load on the needle relative to where the needle is in a suturing stroke.

* * * * *